(12) United States Patent
Moon et al.

(10) Patent No.: US 9,339,354 B2
(45) Date of Patent: *May 17, 2016

(54) MEMBRANE FOR ALVEOLAR BONE REGENERATION

(75) Inventors: Jong Hoon Moon, Busan (KR); Si Young Jung, Busan (KR); Tae Gwan Eom, Busan (KR); Kyoo Ok Choi, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/235,623

(22) PCT Filed: Jul. 20, 2012

(86) PCT No.: PCT/KR2012/005794
§ 371 (c)(1),
(2), (4) Date: Jan. 28, 2014

(87) PCT Pub. No.: WO2013/019007
PCT Pub. Date: Feb. 7, 2013

(65) Prior Publication Data
US 2014/0199657 A1 Jul. 17, 2014

(30) Foreign Application Priority Data

Jul. 29, 2011 (KR) .................. 10-2011-0076172
Aug. 5, 2011 (KR) .................. 10-2011-0078208

(51) Int. Cl.
*A61C 8/02* (2006.01)
*A61F 2/28* (2006.01)
(Continued)

(52) U.S. Cl.
CPC ............. *A61C 8/0006* (2013.01); *A61F 2/2803* (2013.01); *A61F 2/2846* (2013.01);
(Continued)

(58) Field of Classification Search
CPC ..... A61C 8/006; A61F 2/2803; A61F 2/2846; A61L 31/04
USPC ............................................. 623/17.17–17.19
See application file for complete search history.

(56) References Cited

U.S. PATENT DOCUMENTS 6,171,106 B1    1/2001  Kaneko et al.
2005/0192675 A1  9/2005  Robinson
(Continued)

FOREIGN PATENT DOCUMENTS

CN    1464782 A      12/2003
GB    2186000 A  *   8/1987
(Continued)

OTHER PUBLICATIONS

Machine Generated English Translation of Siwon Co. Ltd., Publication No. KR 10-1061758 B1; Nov. 2, 2011.*
(Continued)

*Primary Examiner* — Marcia Watkins
(74) *Attorney, Agent, or Firm* — Ladas & Parry LLP

(57) ABSTRACT

A membrane for alveolar bone regeneration to guide bone generation by adapting to a bone graft material, which fills a bone defect area, includes a central hole through which an implant is inserted into an alveolar bone, wherein the membrane includes: a coupling part to couple the membrane with the implant; a side bending part that is downwardly bent from the coupling part to have an overall curved shape with a gentle slope; and lateral covering parts that protrude from edges of the side bending part and are bent and curved toward an alveolar bone defect area, wherein the side bending part and the lateral covering parts are pre-formed in three-dimensions to fit a final shape of the alveolar bone that is to be regenerated.

38 Claims, 15 Drawing Sheets

(51) Int. Cl.
*A61L 31/04* (2006.01)
*A61L 31/08* (2006.01)
*A61F 2/30* (2006.01)

(52) U.S. Cl.
CPC .............. *A61L 31/04* (2013.01); *A61L 31/088* (2013.01); *A61F 2002/30784* (2013.01); *A61F 2310/00532* (2013.01); *A61L 2430/02* (2013.01)

(56) References Cited

U.S. PATENT DOCUMENTS

| | | |
|---|---|---|
| 2007/0269769 A1 | 11/2007 | Marchesi |
| 2010/0112522 A1 | 5/2010 | Kwon |

FOREIGN PATENT DOCUMENTS

| | | |
|---|---|---|
| JP | 2000-083971 A | 3/2000 |
| JP | 2010-284248 A | 12/2010 |
| KR | 10-0970341 B1 | 7/2010 |
| KR | 10-1061758 B1 | 9/2011 |
| TW | 200520733 A | 7/2005 |
| WO | 01/67987 A1 | 9/2001 |
| WO | 2005092236 A1 | 10/2005 |
| WO | 2005105164 A1 | 10/2005 |
| WO | 2006051401 A2 | 5/2006 |
| WO | 2009137947 A1 | 11/2009 |

OTHER PUBLICATIONS

KIPO Notice of Allowance dated Feb. 24, 2012 Appln. No. 10-2011-0078208 in English.
KIPO Notice of Allowance dated Aug. 28, 2012 Appln. No. 10-2011-0076172 in English.
Japanese Office Action Appln. No. 2014-522741; Dated Dec. 4, 2014.
International Search Report Issued Jul. 27, 2012; Appln. No. 101127281.
First Taiwan Office Action Issued Aug. 15, 2014; Appln. No. 10321120670.
Extended European Search Report Appln. No. 12819865.2-1658/2737871 PCT/KR2012005794; Dated Apr. 20, 2015.
First Chinese Office Action issued Sep. 30, 2015; Appln. No. 201280038257.5.

* cited by examiner

MEMBRANE FOR ALVEOLAR BONE REGENERATION

TECHNICAL FIELD

The present invention relates to a membrane for alveolar bone regeneration that is disposed on a bone defect area and adapts to a graft material to guide bone regeneration, and more particularly, to a membrane for alveolar bone regeneration enabling reduced operation time and convenient manufacture as no local area excessively protrudes since separate trimming and bending are unnecessary and enabling a high success rate of the operation by preventing failure of an alveolar bone regeneration due to a surgical exposure.

BACKGROUND ART

Among non-absorptive materials, a four-sided perforated titanium plate has been generally used for a conventional guided bone regeneration (GBR) technique.

In the conventional GBR technique, a practitioner first recognizes a shape of a location where a bone defect has occurred, appropriately trims the four-sided membrane to a desired shape, adapts to the defect area by three-dimensionally bending the four-sided membrane, and lastly uses a separate screw to fix the four-sided membrane.

However, after recognizing the shape of the bone defect, the conventional GBR technique includes trimming of the membrane to a desired shape and bending of the membrane later, and thus the bone defect area may not be completely adapted and an operation time may be increased. Also, due to an excessive crumpling phenomenon during the bending process, that is, the local area being bent excessively protrudes, the protruded area breaks through gingiva during a period of guiding bone regeneration. Then, the area is infected from the outside and becomes a main factor for bone regeneration failure. Moreover, a large area is required to be incised to remove the screw that is implanted to fix the membrane, and thus, an operation time may be increased, and swelling may occur due to bleeding, which may be painful to a patient. Therefore, the operation has been burdensome to both practitioners and patients.

DETAILED DESCRIPTION OF THE INVENTION

Technical Problem

The present invention provides a membrane for alveolar bone regeneration that is customized by predicting a bone defect shape, wherein the membrane is three-dimensionally trimmed and bent at the same time to avoid local protrusion, and more particularly to, a membrane for alveolar bone regeneration that enables reduced operation time, convenient manufacture, high operation success rate, and less swelling and pain to a patient at the same time.

Technical Solution

According to an aspect of the present invention, there is provided a membrane for alveolar bone regeneration to guide bone generation by adapting to a bone graft material, which fills a bone defect area, wherein the membrane for alveolar bone regeneration includes a coupling part including a central hole through which an implant is inserted into an alveolar bone; a side bending part that is downwardly bent from the coupling part to have an overall curved shape with a gentle slope; and lateral covering parts that protrude from lateral portions of the side bending part and are bent and curved toward an alveolar bone defect area, wherein the side bending part and the lateral covering parts are pre-formed in three-dimensions to fit a final shape of the alveolar bone that is to be regenerated.

The lateral covering parts may be easier to bend than the side bending part.

A plurality of first holes may be formed in the side bending part, and a plurality of second holes may be formed in the lateral covering parts.

The side bending part may include a first bending part that is bent in a direction away from the coupling part and a second bending part that is bent in a direction towards the coupling part.

The first holes may only be formed in the first bending part.

The first holes at the lowermost part of the first bending part may be aligned in a concave dish shape.

A diameter of the first holes may be greater than a diameter of the second holes.

A total hole area of the first holes in the side bending part per unit area may be smaller than a total hole area of the second holes in the side bending part per unit area.

A diameter of the first holes may be in a range of about 0.9 mm to about 2.0 mm, and a diameter of the second holes may be in a range of about 0.1 mm to about 0.5 mm.

The membrane for alveolar bone regeneration may further include lower covering parts that protrude downward from a lower portion of the side bending part and bent inwardly.

A plurality of third holes may be formed in the lower covering parts.

The first holes may be formed in the side bending part, and a diameter of the third holes may be smaller than a diameter of the first holes.

At least two of the lower covering parts may be separated at an equal interval.

The lower covering parts may be symmetrically disposed about a center axis of the side bending part.

The lower covering parts may be pre-formed in three-dimensions to fit a final shape of the alveolar bone that is to be regenerated.

A plurality of fourth holes may be formed in the coupling part.

The membrane for alveolar bone regeneration may further include coupling lateral covering parts protruding from lateral portions of the coupling part and bent to cover the bone graft material.

A plurality of fifth holes may be formed in the coupling lateral covering parts.

The membrane for alveolar bone regeneration may further include coupling upper covering parts protruding from an upper portion of the coupling part and bent to cover the bone graft material.

A plurality of sixth holes may be formed in the coupling upper covering parts.

At least two of the coupling upper covering parts may be separated at an equal interval.

The coupling upper covering parts may be symmetrically disposed about a center axis of the coupling part.

The coupling upper covering parts may be pre-formed in three-dimensions to fit a final shape of the alveolar bone that is to be regenerated.

A surface of the membrane for alveolar bone regeneration may be coated with a tin-coating layer, anodized, or heat-treated to realize various colors.

According to another aspect of the present invention, there is provided a membrane for alveolar bone regeneration to guide alveolar bone regeneration of an alveolar bone defect area by covering an opened wall of the alveolar bone defect area, wherein the membrane for alveolar bone regeneration includes a body part covering the alveolar bone defect area; and protruding parts protruding from the body part and including a concave groove that is concave in a direction towards the body part, wherein if the largest protrusion height of the protruding parts is referred to as $h_1$ and the largest depth of the concave groove is referred as $h_2$, the largest protrusion height $h_1$ is greater than the largest depth $h_2$, thus a crumpling phenomenon occurring during a bending process of the protruding parts from the body part as one region of the protruding parts protrudes more than other regions can be prevented.

The concave grooves may be concave in an opposite direction to a protruding direction of the protruding parts.

Any one of the protruding parts may include a pair of bending lines that are separate from each other, wherein one of the bending lines is formed at a borderline of the body parts and the protruding parts, and the other bending line is formed to meet a bottom of the concave groove.

The body parts may include a coupling part that enables the membrane to couple with an implant; and a side bending part that is bent from the coupling part to cover a side of the alveolar bone.

A central hole through which an implant may be inserted into the alveolar bone is formed in the coupling part.

A plurality of first holes with a smaller diameter than the central hole may be formed in the side bending part.

The side bending part may include a first bending part that is bent in a direction away from the coupling part and a second bending part that is bent in a direction towards the coupling part.

The first holes at the lowermost part of the first bending part may be aligned along a concave line of a "C" shape.

The protruding parts may include coupling upper covering parts that protrude from an upper portion of the coupling part.

The protruding parts may include coupling lateral covering parts that protrude from lateral portions of the coupling part.

The protruding parts may include lateral covering parts that protrude from lateral portions of the side bending part.

A plurality of second holes with a smaller diameter than the first holes may be formed in the lateral covering parts.

A diameter of the first holes may be in a range of about 0.9 mm to about 2.0 mm, and a diameter of the second holes may be in a range of about 0.1 mm to about 0.5 mm.

The protruding parts may include lower covering parts that protrude from a bottom portion of the side bending part.

A plurality of third holes with a smaller diameter than the first holes may be formed in the lower covering parts.

A diameter of the first holes may be in a range of about 0.9 mm to about 2.0 mm, and a diameter of the third holes may be in a range of about 0.6 mm to about 0.8 mm.

A surface of the membrane for alveolar bone regeneration may be coated with a tin-coating layer, anodized, or heat-treated to realize various colors.

The membrane may be pre-formed in a three-dimensional stereoscopic curve shape in a direction of the alveolar bone so as to fit a final shape of an alveolar bone to be regenerated.

Advantageous Effects

A membrane for alveolar bone regeneration according to an aspect of the present invention enables easy, rapid, and convenient operation for a practitioner so that a clinical success rate may be increased, and enables reduced operation time for a patient so that swelling may be reduced. Also, as the burdensome operation time is reduced, both the practitioner and the patient may be satisfied.

Particularly, a membrane for alveolar bone regeneration that are pre-formed in three-dimensions to fit various shapes of bone defects, compared to the conventional products, is provided, thus additional processes, such as trimming and bending, may be minimized, and a protruding phenomenon due to bending of the membrane may be minimized, thus failure of alveolar bone regeneration due to the exposure may be prevented. Therefore, an overall degree of operation completeness may be increased.

BEST MODE

Hereinafter, membranes for alveolar bone regeneration according to exemplary embodiments of the present invention will be described in greater detail with reference to the attached drawings.

Figure 1:
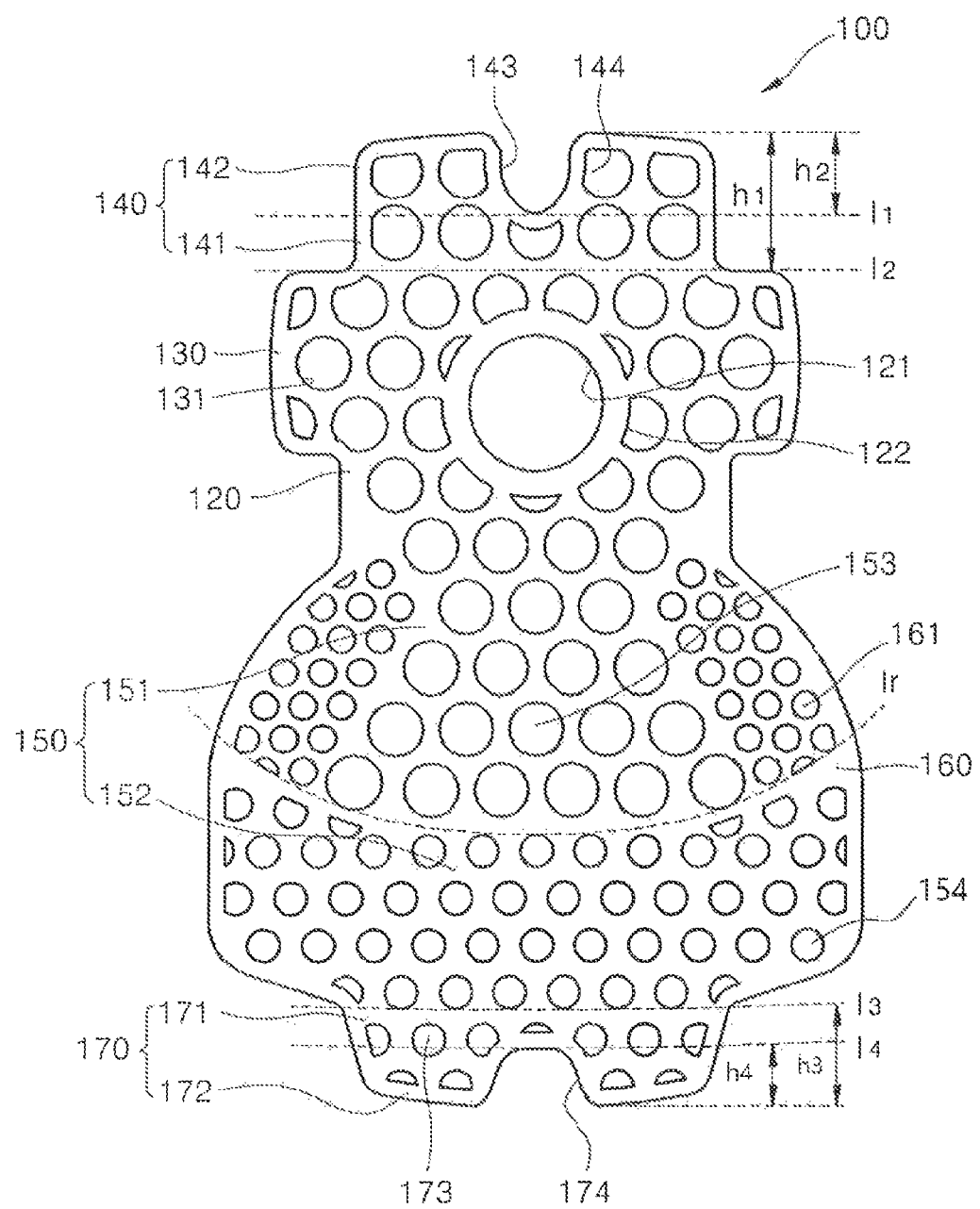
FIG. 1 is a two-dimensional plan view of a membrane for alveolar bone regeneration according to an embodiment of the present invention.
Figure 2:
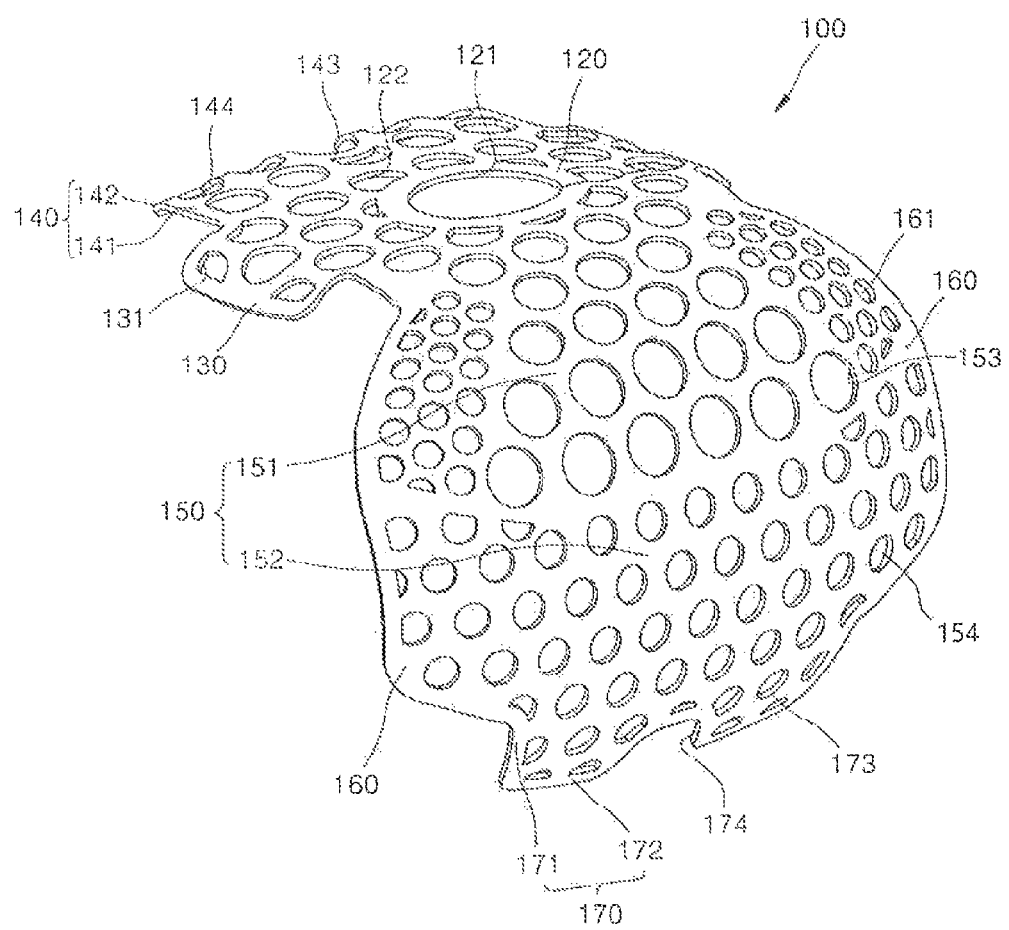
FIGS. 2 and 3 are views of the membrane for alveolar bone regeneration of FIG. 1 that is three-dimensionally formed.
Figure 3:
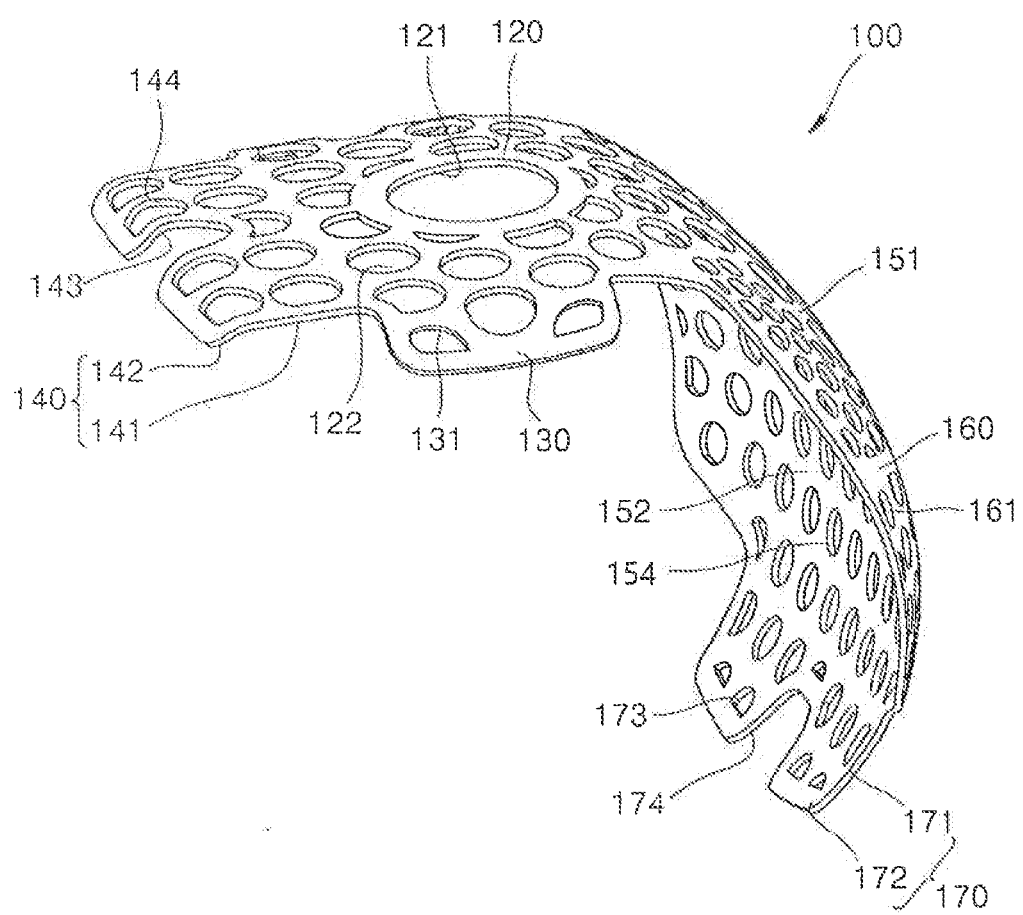
Figure 4:
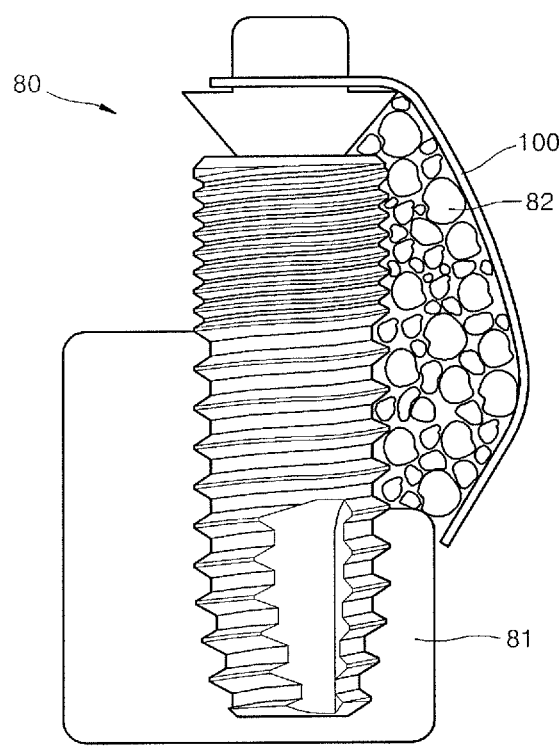
FIG. 4 is a view of the membrane for alveolar bone regeneration of FIG. 1 that is operated.

A membrane for alveolar bone regeneration 100 according to an embodiment of the present invention covers an opened wall of an alveolar bone defect area to guide the alveolar bone regeneration at the alveolar bone defect area. The two-dimensional plan view of the membrane for alveolar bone regeneration 100 of FIG. 1 illustrates that a shape of the membrane for alveolar bone regeneration 100 is trimmed to fit the shape of a bone defect that is pre-recognized. FIGS. 2 and 3 illustrate a shape of the pre-trimmed two-dimensional membrane for alveolar bone regeneration 100 that is three dimensionally bent with a predetermined bending device.

In this regard, the membrane for alveolar bone regeneration 100 according to an embodiment of the present invention is manufactured by performing three-dimensional trimming and bending in advance by using the predetermined bending device, rather than a practitioner instantly trimming and bending a membrane to fit the shape of the bone defect of a patient right before the operation. Thus, the membrane for alveolar bone regeneration 100 is characterized as being formed in advance into a shape with a stereoscopically surface curved in a direction of an alveolar bone to fit the alveolar bone, which is to be regenerated.

The membrane for alveolar bone regeneration 100 includes body parts and protruding parts. Here, the body parts, which may cover the alveolar bone defect area, include a coupling part 120 and a side bending part 150. The protruding parts, which protrude by being extended from the body parts, include coupling lateral covering parts 130, coupling upper covering parts 140, lateral covering parts 160, and lower covering parts 170. Here, if the largest protrusion height of the protruding parts is referred to as $h_1$ and the largest depth of a concave groove 143 is referred as $h_2$, the largest protrusion height $h_1$ is greater than the largest depth $h_2$, thus a crumpling phenomenon, which occurs when one region of the protruding parts is more protruded than other regions of the protruding parts, may be prevented during a process of bending the protruding parts from the body parts.

The coupling part 120 includes a central hole 121 through which an implant 80 is inserted into an alveolar bone 81, and thus the membrane for alveolar bone regeneration 100 is coupled with the implant 80. The coupling part 120 adapts to an upper portion of a region where a bone graft material 82 is stacked up for the bone defect area with a generally flattened shape. The central hole 121 is formed in a central area of the coupling part 120, and a plurality of fourth holes 122 are distributed in a radial form around the central hole 121. The fourth holes 122 may have a smaller size than the central hole 121. The fourth holes 122 enable the bone graft material 82 to firmly and stably bone fuse with peripheral bone tissue by activating a physiological reaction between the bone graft material 82 filling the bone defect area and blood of the peripheral bone tissue, and thus, a size of the fourth holes 122 may be an appropriate size for the bone fusion.

The coupling lateral covering parts 130, which are curved from the coupling part 120 to cover sides of the bone graft material 82, protrude from lateral portion of the coupling part 120. The coupling lateral covering parts 130 may be curved downward to cover the bone graft material 82. The coupling lateral covering parts 130 may be formed protruding from parts of the lateral portion of the coupling part 120, and accordingly, the bending of the coupling lateral covering parts 130 may be conveniently performed. In particular, the coupling lateral covering parts 130 are provided to adapt to a mesial or distal side of the alveolar bone, and the coupling lateral covering parts 130 are formed to extend in a direction toward a neighboring tooth.

The coupling lateral covering parts 130 include a plurality of fifth holes 131. The fifth holes 131 may have shape of a circle or an irregular circle. Also, the fifth holes 131 may have a smaller diameter than the fourth holes 122, if necessary. Accordingly, a greater number of holes may be formed in a small area. In this regard, overall flexibility increases and the bending may be conveniently performed as the number of fifth holes 131 increases.

The coupling upper covering parts 140, which are disposed on the coupling part 120, may be curved inwards to cover the bone graft material 82. Two of the coupling upper covering parts 140 may be disposed side by side, and the coupling upper covering parts 140 may be symmetrical about a center axis of the concave groove 143 formed in the middle of the two coupling upper covering parts 140. Here, the concave groove 143 has a concave shape in a direction towards the body parts from upper portion of the coupling upper covering parts 140, and thus the concave groove 143 may be concave toward an opposite direction from a protrusion direction of the coupling upper covering parts 140. That is, as shown in FIG. 1, the coupling upper covering parts 140 protrude upward from the coupling parts 120, while the concave groove 143 may be concave downward the coupling upper covering parts 140. Here, if the largest protrusion height of the coupling upper covering parts 140, which are also the protruding parts, is referred to as $h_1$ and the largest depth of the concave groove 143 is referred as $h_2$, the largest protrusion height $h_1$ is greater than the largest depth $h_2$. In addition, a pair of bending lines may be separated from each other on the coupling upper covering parts 140, which are also the protruding parts. Here, among the bending lines, one bending line $l_2$ (also referred to as "second bending line") may be formed at a borderline of the coupling part 120, which is one of the body parts, and the coupling upper covering parts 140, which are also the protruding parts, and the other bending line $l_1$ (also referred to as "first bending line") may be formed to meet a bottom of the concave groove 143.

Here, the bending line $l_2$ may connect a pair of second bending points where the coupling part 120 and the coupling upper covering parts 140 meet, and the other bending line may be separately located above the second bending points and passes an bottom point of the concave groove 143. Here, the bending line $l_1$ may be located above and parallel to the bending line $l_2$.

The coupling upper covering parts 140 may be divided into a first upper part 141 including each part of the coupling upper covering parts 140 and second upper parts 142 both protruding from the first upper part 141, wherein the concave groove 143 is formed between the second upper parts 142. In this regard, the first upper part 141 may be primarily bent along the second bending line $l_2$, and then the second upper part 142 may be secondarily bent along the first bending line during a process of bending the coupling upper covering parts 140 from the coupling part 120, which is one of the body parts. Here, the primary bending and the secondary bending may be separately performed, but the processes are not limited thereto and may occur simultaneously and spontaneously. In this regard, as the secondary bending is performed, a whole bending curve line may have a gentle slope, and thus a crumpling phenomenon locally occurring at an area where the bending processes start may be prevented. Also, even when only one of the bending processes is performed, the overall curve may have a gentle slope, and thus the crumpling phenomenon, which occurs when one region protrudes more than other regions, may be prevented.

In addition, the coupling upper covering parts 140 may include a plurality of sixth holes 144, and the bone fusion may be enhanced as blood flows through the sixth holes 144.

The side bending part 150, which is downwardly bent from the coupling part 120 to be curved, may cover a side of the alveolar bone. The side bending part 150 after bending has an overall curved shape with a gentle slope. The side bending part 150 includes a plurality of first holes 153 with a predetermined size. The first holes 153 are used as pathways for blood to flow as mentioned above.

The side bending part 150 includes a first bending part 151 that may be bent in a direction away from the coupling part 120 and a second bending part 152 bending in a direction towards the coupling part 120. Here, the first bending part 151 may include the first holes 153 with a diameter in a range of about 0.9 mm to about 2.0 mm, and the second bending part 152 may include seventh holes 154 with a diameter smaller than that of the first holes 153 of the first bending part 151. Here, the first holes 153 at the lowermost part of the first bending part 151 may be aligned along a concave line Ir of a "C" shape. In this regard, the first holes 153 are aligned in a "C" shape to spontaneously form a bending line as the concave line Ir, and thus localized protrusion at some regions during a bending process may be prevented. Also, a size of the seventh holes 154 of the second bending part 152 is relatively small to maximize the flexibility of the side bending part 150 during the bending process, so that the side bending part 150 may be bent to be curved even when a radius of curvature is large.

The lateral covering parts 160, in which the bone graft material 82 may be provided, is formed to protrude from a lateral portion of the side bending part 150 and may be bent toward the bone graft material 82 to be curved. The lateral covering parts 160 include a plurality of second holes 161. The lateral covering parts 160 cover a buccal side of the bone defect area and may have a shape having a distance between the side bending part 150 gradually increasing from an upper portion to a lower portion of the lateral covering parts 160 and maintaining a constant distance between the side bending part 150 which after a midline of the lateral covering parts 160. Each of the lateral covering parts 160 is made as a single unit throughout the entire lateral portion of the side bending part 150 so as that the lateral covering parts 160 may be conveniently removed from the bone defect area after the bone fusion. The plurality of second holes 161 are formed in the lateral covering parts 160, and a diameter of the second holes 161 may be smaller than that of the first holes 153. For example, a diameter of the first holes 153 may be in a range of about 0.9 mm to about 2.0 mm, and a diameter of the second holes 161 may be in a range of about 0.1 mm to about 0.5 mm. Here, the second holes 161 may be more tightly arranged than the first holes 153, thus a greater number of holes may be formed in the lateral covering parts 160 per the same unit area. That is, a total hole area of the second holes 161 per unit area of the lateral covering parts 160 may be larger than a total hole area of the first holes 153 per unit area of the side bending part 150.

In this regard, as the second holes 161 are tightly arranged with a small diameter, the overall flexibility of the lateral covering parts 160 increases, and thus the membrane for alveolar bone regeneration 100 may be conveniently removed from the alveolar bone 81 without damaging nearby gingiva after completion of the alveolar bone regeneration. Also, as the lateral covering parts 160 are flexible, the bending may be conveniently performed.

The lower covering parts 170 protrude downward from a lower portion of the side bending part 150. The lower covering parts 170 include a plurality of third holes 173. A diameter of the third holes 173 may be smaller than that of the first holes 153. For example, a diameter of the first holes 153 may be in a range from about 0.9 mm to about 2.0 mm, and a diameter of the third holes 173 may be in a range from about 0.6 mm to about 0.8 mm. Accordingly, the lower covering parts 170 may obtain sufficient flexibility, and thus the lower covering parts 170 may be removed from the alveolar bone 81 after a subsequent bone fusion.

The lower covering parts 170 may include a concave groove 174 that is concave in a direction toward the body parts, and if the largest protrusion height of the lower covering parts 170, which are also the protruding parts, is referred to as $h_3$ and the largest depth of the concave groove 174 is referred as $h_4$, the largest protrusion height $h_3$ is greater than the largest depth $h_4$. In addition, a pair of bending lines may be separated from each other on the lower covering parts 170, which are also the protruding parts. Here, among the bending lines, one bending line 13 may be formed at a borderline of the side bending part 150, which is one of the body parts, and the lower covering parts 170, which are also the protruding parts, and the other bending line $l_4$ may be formed to meet a bottom of the concave groove 174.

Here, the bending line 13 may connect a pair of third bending points (not shown) where the side bending part 150 and the lower covering parts 170 meet, and the other bending line $l_4$ may be separately located above the third bending points and passes an bottom point (not shown) of the concave groove 174. Here, the bending line $l_3$ may be located above and parallel to the bending line $l_4$, but is not limited there to, and the bending line $l_3$ may be separated unparallel to the bending line $l_4$.

Here, the lower covering parts 170 include a first lower covering part 171 and second lower covering parts 172, wherein the first lower covering part 171 extends continuously along both of the lower covering parts 170, and the second lower covering parts 172 are both protruded from the first lower covering part 171 to be bent individually. As the bending lines $l_3$ and $l_4$ separated from each other, an overall bending line may have a gentle slope, and thus a local protruding phenomenon may be prevented. That is, when there is only one bending line, the lower covering parts 170 may be curved at a steep angle, thus a crumpling phenomenon around the bending line may excessively occur. However, when there are two or more bending lines as described in the current embodiment of the present invention, the lower covering parts 170 may be curved at a relatively shallow angle, thus localized stress concentration may hardly occur, and accordingly, the drastic crumpling phenomenon at some regions may be prevented.

In addition, a surface of the membrane for alveolar bone regeneration 100 may be coated with a tin-coating layer, anodized, or heat-treated to realize various colors. Here, when the surface of the membrane for alveolar bone regeneration 100 is anodized, the surface of the membrane for alveolar bone regeneration 100 may realize various surface colors by changing an applied voltage. Also, when the surface of the membrane for alveolar bone regeneration 100 is heat-treated, various colors, such as a gold color, may be realized according to a heat-treating temperature. In this regard, the membrane for alveolar bone regeneration 100 may be realized with various colors when the surface is coated with a tin-coating layer, anodized, or heat-treated, and thus, an overall aesthetic sense may be improved. Moreover, as shown in FIGS. 2 and 3, the membrane for alveolar bone regeneration 100 may be pre-formed in a three-dimensional stereoscopic curve shape in a direction of the alveolar bone 81 as to fit a final shape of an alveolar bone to be regenerated.

The membrane for alveolar bone regeneration 100 according to the current embodiment of the present invention has the following effects.

First, before attaching the membrane for alveolar bone regeneration 100, the implant 80 is inserted to the alveolar bone 81, and the bone graft material 82 is filled in the bone defect area. Then, the membrane for alveolar bone regeneration 100 pre-formed by a three-dimensionally forming process for the implant 80 is coupled to the implant 80. In particular, the pre-formed membrane for alveolar bone regeneration 100 is coupled to the implant 80 by screwing the implant 80 through the central hole 121 of the coupling part 120. After the membrane for alveolar bone regeneration 100 is fix-coupled in the manner described above, the defect area is adapted to gingiva. Then, a predetermined time passes for the bone graft material 82 to be bone fused to the membrane for alveolar bone regeneration 100. Thus, after the alveolar bone is regenerated, the membrane for alveolar bone regeneration 100 is removed from the bone defect area.

An overall bending line of the membrane for alveolar bone regeneration 100 according to an embodiment of the present invention may have a gentle slope as the pair of bending lines $l_3$ and $l_4$, which are separated from each other, are formed on the lower covering parts 170, and thus a crumpling phenomenon may be prevented. For example, as shown in FIGS. 2 and 3, the pair of bending lines $l_3$ and $l_4$ of the lower covering parts 170 may prevent the crumpling phenomenon (occurrence), may enable complete adhesion of the membrane for alveolar bone regeneration 100 to the bone graft material 82 during a guiding period of the bone regeneration, and may serve as a stable guide, thus a risk of the membrane for alveolar bone regeneration 100 being exposed through the gingival may be minimized.

Moreover, the flexibility at a region where a steep curve is necessary may be increased by varying the sizes of the holes for each region, and thus bendability may be maximized. Accordingly, a field usability at the operation field may be increased even when local bending is necessary.

Also, as the lateral covering parts 160 are designed to have high flexibility, the membrane for alveolar bone regeneration 100 may be convenient to be later removed from a bone graft material, in addition to its bendability.

Moreover, the membrane for alveolar bone regeneration 100 may be pre-formed in a three-dimensional stereoscopic curve shape in a direction of the alveolar bone 81 as to fit a final shape of an alveolar bone to be regenerated by using a predetermined bending device, and accordingly, the crumpling phenomenon may be certainly prevented instead of forming a membrane at an instance.

Figure 5:
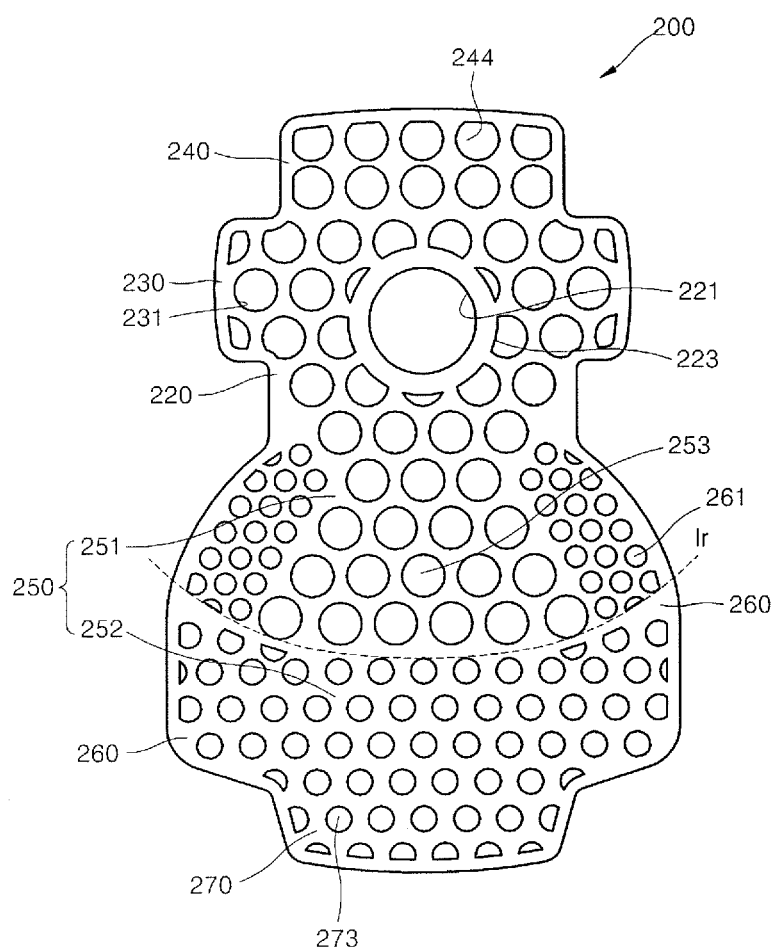
FIGS. 5 through 15 are two-dimensional views of membranes for alveolar bone regeneration according to embodiments of the present invention.

A membrane for alveolar bone regeneration according to an embodiment may be modified as follows:

First, as shown in FIG. 5, a membrane for alveolar bone regeneration 200 may not have separate concave grooves in coupling upper covering parts 240 and lower covering parts 270.

Other major parts of the membrane for alveolar bone regeneration 200 may have substantially the same structure as the membrane for alveolar bone regeneration 100 shown in FIGS. 1 through 4.

Figure 6:
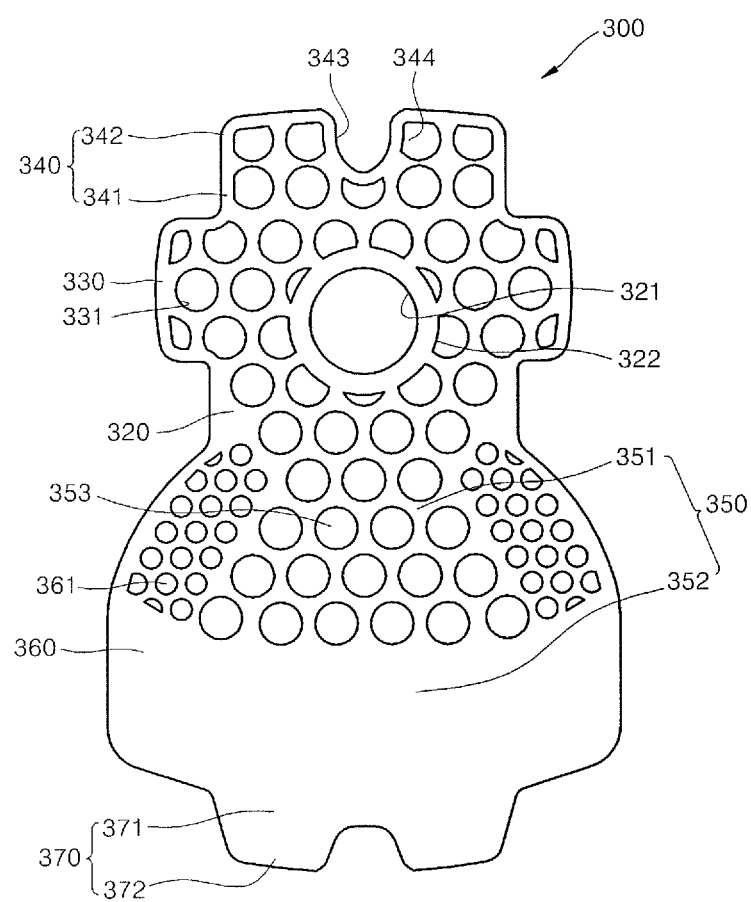

Also, as shown in FIG. 6, separate holes may not be formed in a second bending part 352 and lower covering parts 370. In this regard, a membrane for alveolar bone regeneration 300 may be conveniently as separate holes are not formed in the second bending part 352 and the lower covering parts 370. For example, when separate holes are not formed in the second bending part 352 and the lower covering parts 370, blood may not flow through, and accordingly, linkage tissue due to the blood flow may not be provided, and thus the membrane for alveolar bone regeneration 300 may be conveniently removed from the bone graft material later.

Figure 7:
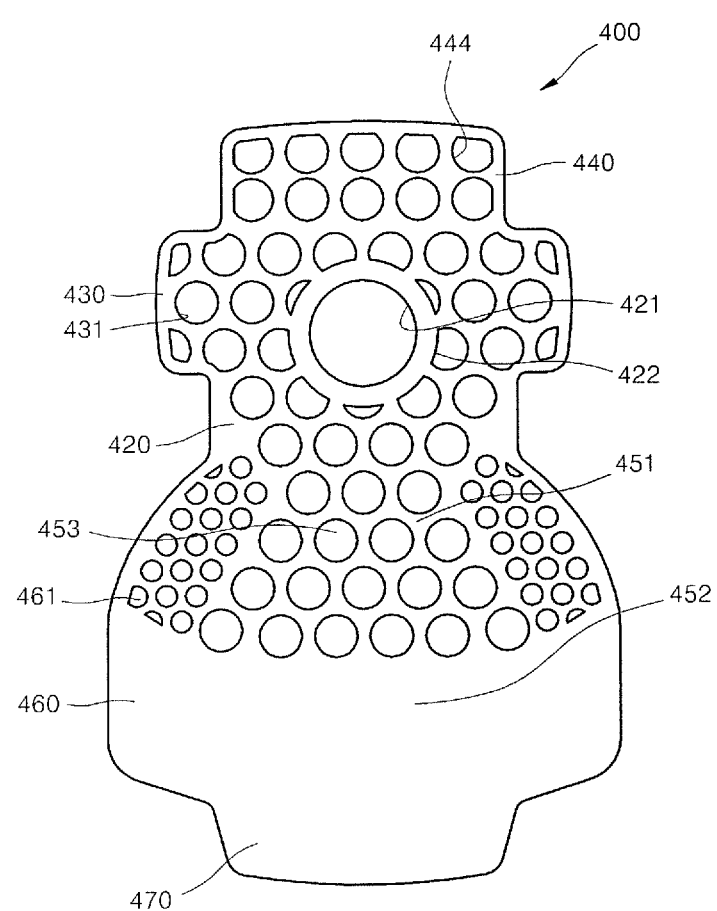

Moreover, as shown in FIG. 7, separate holes may not be formed in a second bending part 452 and a lower covering part 470 of a membrane for alveolar bone regeneration 400. Although an overall structure of the membrane for alveolar bone regeneration 400 is substantially the same as the membrane for alveolar bone regeneration 200 shown in FIG. 5, the membrane for alveolar bone regeneration 400 may be conveniently removed as separate holes are not formed in the second bending part 452 and the lower covering part 470.

Figure 8:
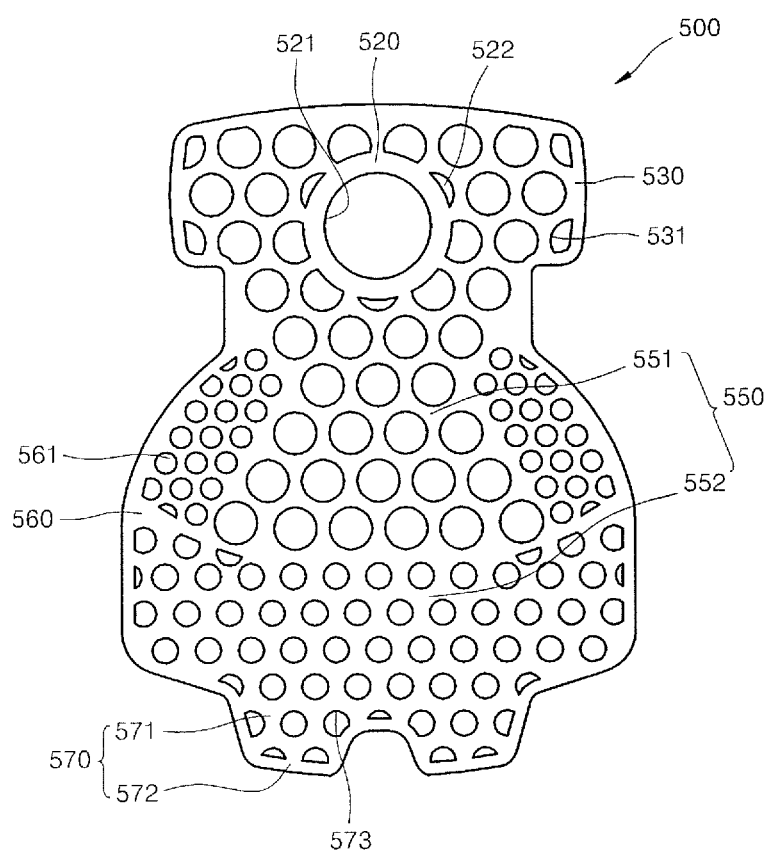

Also, as shown in FIG. 8, separate coupling upper covering parts may not be provided. That is, unlike the membrane for alveolar bone regeneration 100 shown in FIGS. 1 through 4, a membrane for alveolar bone regeneration 500 of FIG. 8, where separate coupling upper covering parts 140 are not provided, may be used when there is no defect on a side where the tongue is located but the defect is on the side of the lips and peripheral teeth.

Figure 9:
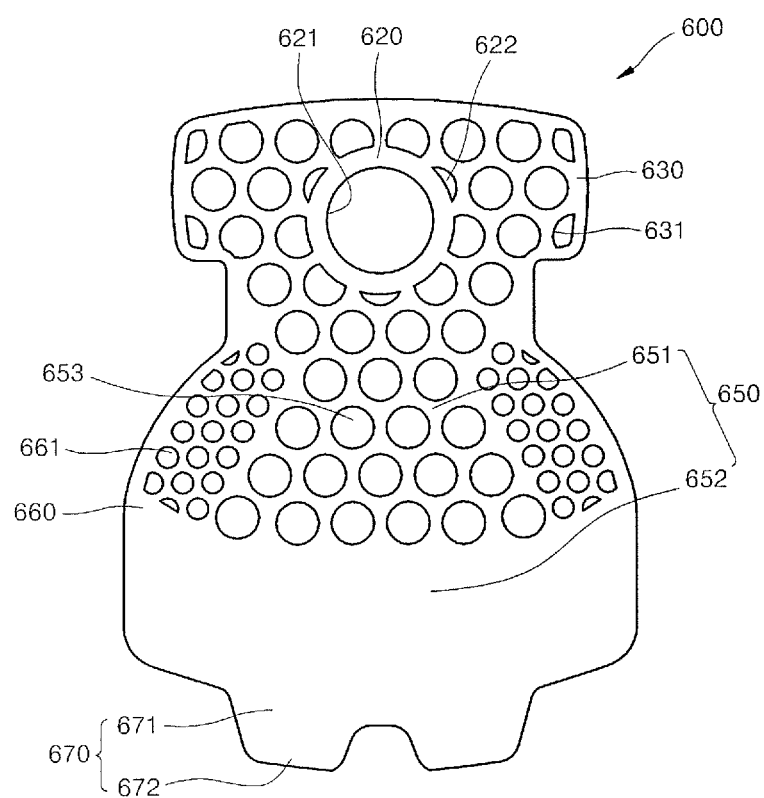

Also, as shown in FIG. 9, separate holes may not be formed in a second bending part 652 and lower covering parts 670. Although an overall structure of a membrane for alveolar bone regeneration 600 is substantially the same as the membrane for alveolar bone regeneration 500 shown in FIG. 5, the membrane for alveolar bone regeneration 600 may be conveniently removed as separate holes are not formed in the second bending part 652 and the lower covering parts 670.

Figure 10:
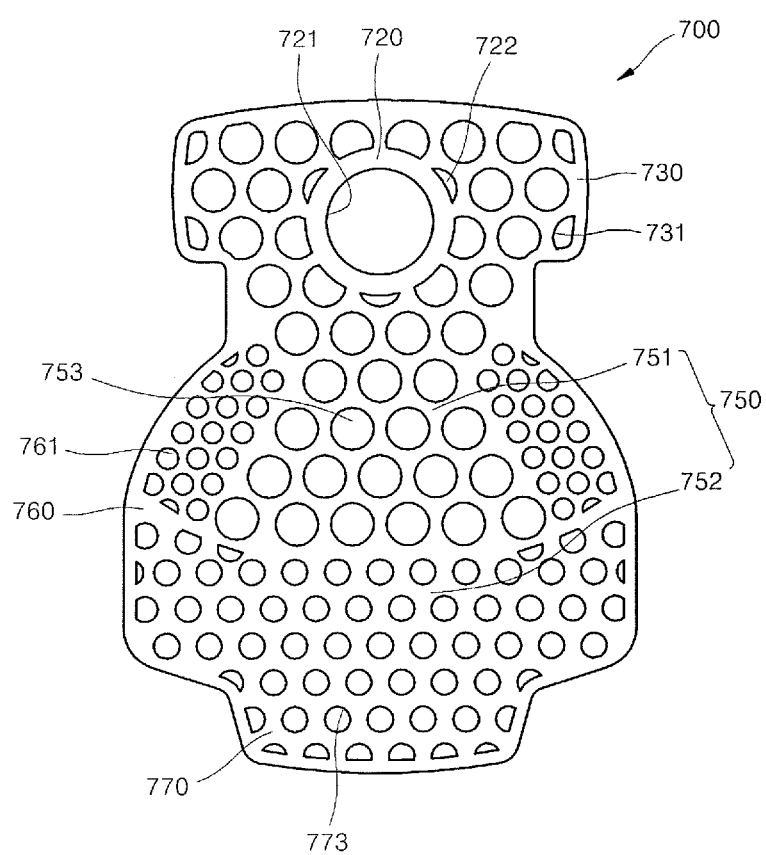

Also, as shown in FIG. 10, separate coupling upper covering parts may not be provided. Although an overall structure is substantially the same as the membrane for alveolar bone regeneration 200 shown in FIG. 5, a membrane for alveolar bone regeneration 700, where separate coupling upper covering parts are not provided, may be used when there is no defect on a side where the tongue is located but the defect is on the side of the lips and peripheral teeth.

Figure 11:
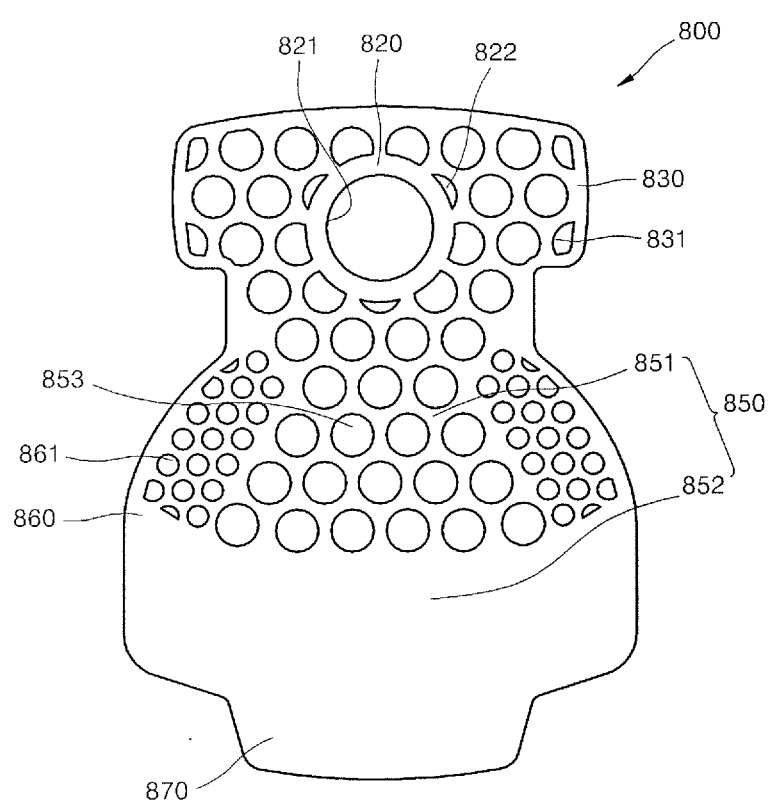

Also, as shown in FIG. 11, separate holes may not be formed in a second bending part 852 and lower covering parts 870. Although an overall structure is substantially the same as the membrane for alveolar bone regeneration 700 shown in FIG. 10, linkage tissue is not formed at the corresponding area when separate holes are not formed in the second bending part 852 and the lower covering parts 870, and thus, the membrane for alveolar bone regeneration 800 may be conveniently removed.

Figure 12:
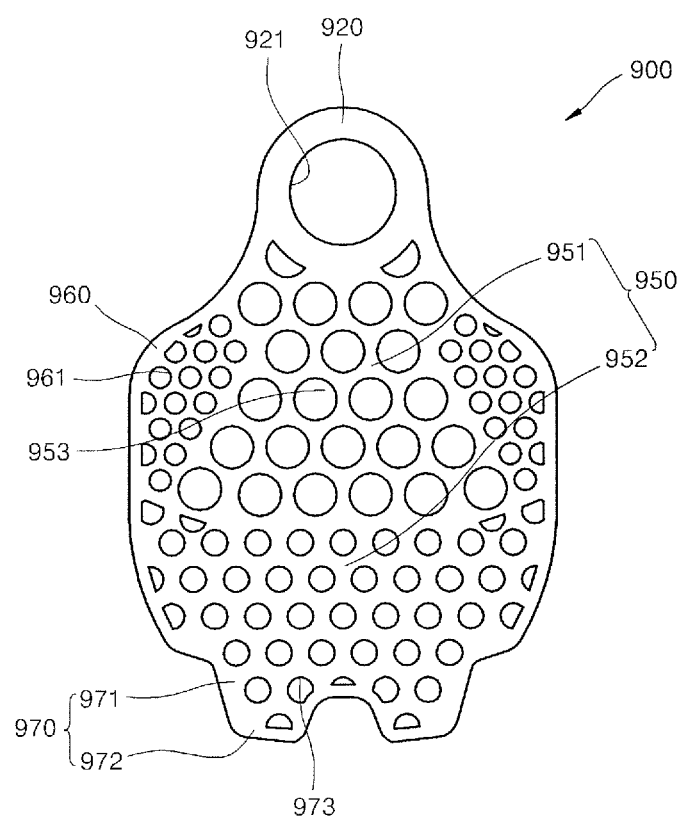

Also, as shown in FIG. 12, the membrane for alveolar bone regeneration 100 may be structured without the coupling lateral covering parts 130 and the coupling upper covering parts 140. In this regard, a membrane for alveolar bone regeneration 900 that is not provided with coupling lateral covering parts and coupling upper covering parts may be used when there is no defect on a side where the tongue and peripheral teeth are located but the defect is on the side of the lips only.

Figure 13:
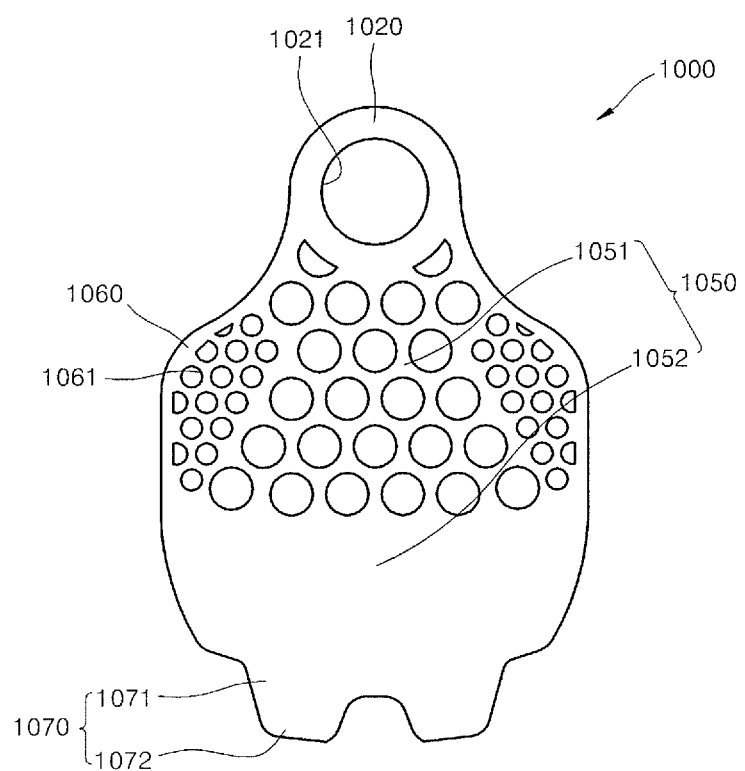

Also, as shown in FIG. 13, separate holes may not be formed in a second bending part 1052 and lower covering parts 1070. In this regard, a membrane for alveolar bone regeneration 1000 where holes are not formed in a certain area may not form linkage tissue at the corresponding area, and thus, the membrane for alveolar bone regeneration 1000 may be conveniently removed.

Figure 14:
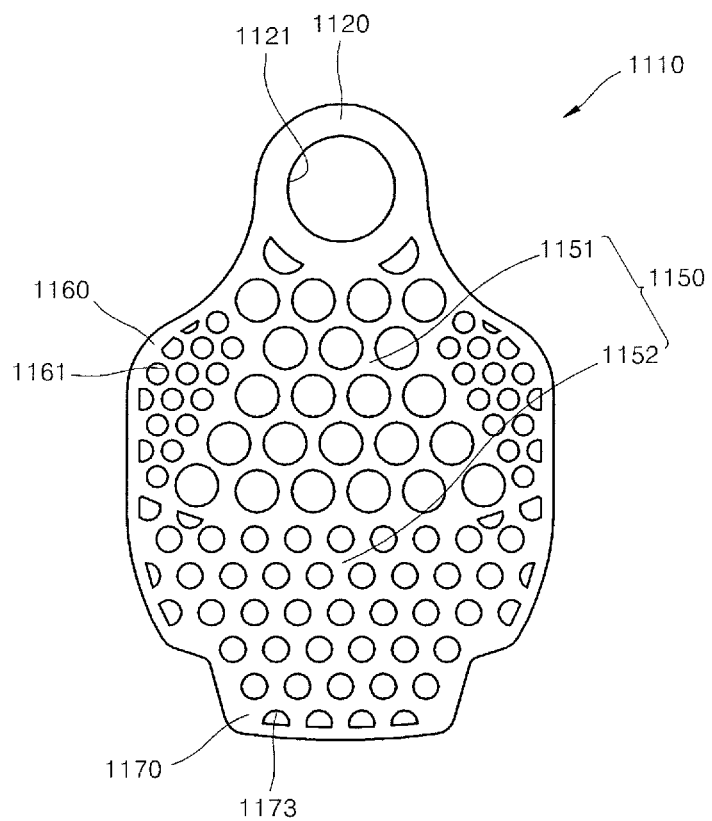

Also, as shown in FIG. 14, a lower covering part 1170 may be formed as one. Although an overall structure is substantially the same as the membrane for alveolar bone regeneration 1000 shown in FIG. 13, an area that may be covered by a membrane may increase if the lower covering part 1170 is formed as one.

Figure 15:
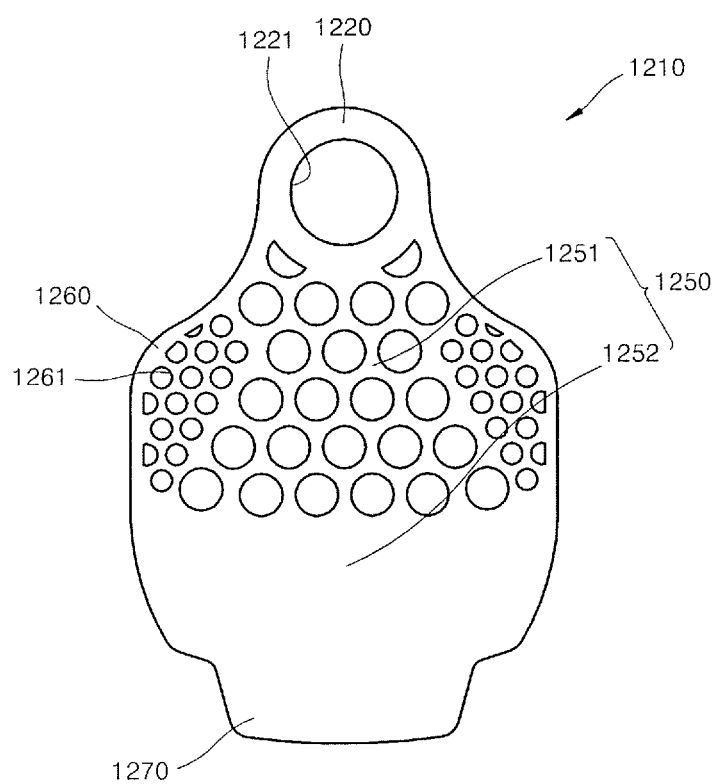

Also, as shown in FIG. 15, separate holes may not be formed in a second bending part 1252 and a lower covering part 1270. Although an overall structure is substantially the same as the membrane for alveolar bone regeneration 1110 shown in FIG. 14, a membrane for alveolar bone regeneration 1210 may be conveniently removed as linkage tissue is not formed at the corresponding area when separate holes are not formed in the second bending part 1252 and the lower covering part 1270.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A membrane for alveolar bone regeneration to guide the alveolar bone regeneration by adapting to a bone graft material, which fills an alveolar bone defect area, the membrane for alveolar bone regeneration comprising:
   a coupling part comprising a central hole that is sized and shaped to allow for an implant to be inserted through the central hole into the alveolar bone that is to be regenerated;
   a side bending part that is downwardly bent from the coupling part to have an overall curved shape; and
   a lateral covering part that protrudes from a lateral portion of the side bending part and is bent and curved toward the alveolar bone defect area,
   wherein the side bending part and the lateral covering part are pre-formed in three-dimensions to fit a final shape of the alveolar bone that is to be regenerated,
   wherein a plurality of first holes are formed in the side bending part, and a plurality of second holes are formed in the lateral covering part, and
   a diameter of the first holes is greater than a diameter of the second holes.

2. The membrane for alveolar bone regeneration of claim 1, wherein the lateral covering part is easier to bend than the side bending part.

3. The membrane for alveolar bone regeneration of claim 1, wherein the side bending part comprises a first bending part that is bent so as to extend from the coupling part in a direction away and downward from the coupling part and a second bending part that is bent so as to extend towards the coupling part.

4. The membrane for alveolar bone regeneration of claim 3, wherein the first holes are only formed in the first bending part.

5. The membrane for alveolar bone regeneration of claim 3, wherein the first holes at a lowermost part of the first bending part are aligned in a concave line shape.

6. The membrane for alveolar hone regeneration of claim 1, wherein a total hole area of the first holes in the side bending part per unit area is smaller than a total hole area of the second holes in the lateral covering part per unit area.

7. The membrane for alveolar bone regeneration of claim 1, wherein the diameter of the first holes is in a range of 0.9 mm to 2.0 mm, and the diameter of the second holes is in a range of 0.1 mm to 0.5 mm.

8. The membrane for alveolar bone regeneration of claim 1, further comprising a lower covering part that protrudes downward from a lower portion of the side bending part and is bent inwardly.

9. The membrane for alveolar bone regeneration of claim 8, wherein a plurality of third holes are formed in the lower covering part.

10. The membrane for alveolar bone regeneration of claim 9, wherein the diameter of the third holes is smaller than the diameter of the first holes.

11. The membrane for alveolar bone regeneration of claim 9, wherein the lower covering part is pre-formed in three-dimensions to fit the final shape of the alveolar bone that is to be regenerated.

12. The membrane for alveolar bone regeneration of claim 8, wherein the lower covering part comprises two lower covering parts which are separated from each other.

13. The membrane for alveolar bone regeneration of claim 12, wherein the two lower covering parts are symmetrically disposed about a center axis of the side bending part.

14. The membrane for alveolar bone regeneration of claim 1, wherein a plurality of fourth holes are formed in the coupling part.

15. The membrane for alveolar bone regeneration of claim 14, further comprising a coupling lateral covering part protruding from a lateral portion of the coupling part and bent so as to be configured for covering the hone graft material.

16. The membrane for alveolar bone regeneration of claim 15, wherein a plurality of fifth holes are formed in the coupling lateral covering part.

17. The membrane for alveolar bone regeneration of claim 1, further comprising coupling upper covering parts protruding from an upper portion of the coupling part and bent so as to be configured for covering the bone graft material.

18. The membrane for alveolar hone regeneration of claim 17, wherein a plurality of sixth holes are formed in the coupling upper covering parts.

19. The membrane for alveolar bone regeneration of claim 17, wherein there are two coupling upper covering parts and the two coupling upper covering parts are separated from each other.

20. The membrane for alveolar bone regeneration of claim 19, wherein the two coupling upper cover parts are symmetrically disposed about a center axis of the coupling part.

21. The membrane for alveolar bone regeneration of claim 17, wherein the coupling upper covering parts are pre-formed in three-dimensions to fit the final shape of the alveolar bone that is to be regenerated.

22. The membrane for alveolar bone regeneration of claim 1, wherein a surface of the membrane for alveolar bone regeneration is coated with a tin-coating layer, anodized, or heat-treated to realize various colors.

23. A membrane for alveolar bone regeneration to guide alveolar bone regeneration of an alveolar bone defect area by covering an opened wall of the alveolar bone defect area, the membrane for alveolar bone regeneration comprising:
    a body part configured for covering the alveolar bone defect area; and
    protruding parts protruding from the body part and comprising a concave groove that is concave in a direction towards the body part,
    wherein if a largest protrusion height of the protruding parts is referred to as h and a largest depth of the concave groove is referred as $h_2$, the largest protrusion height $h_1$ is greater than the largest depth $h_2$, thus a crumpling phenomenon occurring during a bending process of the protruding parts from the body part as one region of the protruding parts protrudes more than other regions can be prevented,
    wherein any one of the protruding parts comprises a pair of bending lines that are separate from each other, wherein one of the bending lines is formed at a borderline of the body part and the protruding part, and the other bending line is formed to meet a bottom of the concave groove.

24. The membrane for alveolar bone regeneration of claim 23, wherein the body part comprises;
    a coupling part that enables the membrane to couple with an implant; and
    a side bending part that is bent from the coupling part so as to be configured for covering a side of the alveolar bone.

25. The membrane for alveolar bone regeneration of claim 24, wherein a central hole is formed in the coupling part, the central hole being sized and shaped to allow for the implant to be inserted through the central hole into the alveolar bone.

26. The membrane for alveolar bone regeneration of claim 25, wherein a plurality of first holes with a smaller diameter than the central hole are formed in the side bending part.

27. The membrane for alveolar bone regeneration of claim 26, wherein the side bending part comprises a first bending part that is bent in a direction away from the coupling part and a second bending part that is bent in a direction towards the coupling part.

28. The membrane for alveolar bone regeneration of claim 27, wherein the first holes at a lowermost part of the first bending part are aligned along a concave line of a "C" shape.

29. The membrane for alveolar bone regeneration of claim 27, wherein a lateral covering part protrudes from a lateral portion of the side bending part.

30. The membrane for alveolar bone regeneration of claim 29, wherein a plurality of second holes with a smaller diameter than the first holes are formed in the lateral covering part.

31. The membrane for alveolar bone regeneration of claim 30, wherein the diameter of the first holes is in a range of 0.9 mm to 2.0 mm, and the diameter of the second holes is in a range of 0.1 mm to 0.5 mm.

32. The membrane for alveolar bone regeneration of claim 26, wherein the protruding parts comprise lower covering parts that protrude from a bottom portion of the side bending part.

33. The membrane for alveolar bone regeneration of claim 32, wherein a plurality of third holes with a smaller diameter than the first holes are formed in the lower covering part.

34. The membrane for alveolar bone regeneration of claim 33, wherein the diameter of the first holes is in a range of 0.9 mm to 2.0 mm, and a the diameter of the third holes is in a range of 0.6 mm to 0.8 mm.

35. The membrane for alveolar bone regeneration of claim 24, wherein at least one protruding part of the protruding parts comprises a coupling upper covering part that protrudes from an upper portion of the at least one protruding part.

36. The membrane for alveolar bone regeneration of claim 24, wherein the membrane further comprises a coupling lateral covering part that protrudes from a lateral portion of the coupling part.

37. The membrane for alveolar bone regeneration of claim 23, wherein a surface of the membrane for alveolar bone regeneration is coated with a tin-coating layer, anodized, or heat-treated to realize various colors.

38. The membrane for alveolar bone regeneration of claim 23, wherein the membrane is pre-formed in a three-dimensional stereoscopic curved shape in a direction of the alveolar bone so as to fit a final shape of the alveolar bone to be regenerated.

\* \* \* \* \*